United States Patent
Keen et al.

(10) Patent No.: US 10,667,765 B2
(45) Date of Patent: Jun. 2, 2020

(54) AUTOMATED SMART WATCH ASSISTANCE IN THE EVENT OF CARDIAC ARREST

(71) Applicant: INTERNATIONAL BUSINESS MACHINES CORPORATION, Armonk, NY (US)

(72) Inventors: Martin G. Keen, Cary, NC (US); Adam Smye-Rumsby, Reading, PA (US); Hernan A. Cunico, Holly Springs, NC (US); Paul A. R. Frank, Berlin (DE)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/992,327

(22) Filed: May 30, 2018

(65) Prior Publication Data

US 2019/0365333 A1 Dec. 5, 2019

(51) Int. Cl.
 *G08B 1/08* (2006.01)
 *A61B 5/00* (2006.01)
 *A61B 5/01* (2006.01)
 *A61B 5/021* (2006.01)

(52) U.S. Cl.
 CPC ............ *A61B 5/747* (2013.01); *A61B 5/0026* (2013.01); *A61B 5/01* (2013.01); *A61B 5/021* (2013.01); *A61B 5/681* (2013.01)

(58) Field of Classification Search
 CPC ....... A61B 5/747; A61B 5/021; A61B 5/0026; A61B 5/01; A61B 5/681
 USPC .................................................... 340/539.12
 See application file for complete search history.

(56) References Cited

U.S. PATENT DOCUMENTS

| | | | |
|---|---|---|---|
| 9,028,259 B2 | 5/2015 | Centen et al. | |
| 9,314,159 B2* | 4/2016 | Lyon | ...................... A61B 5/746 |
| 9,547,972 B2 | 1/2017 | Castillo | |
| 9,942,788 B1* | 4/2018 | Zeine | .................... H04W 40/04 |
| 10,092,236 B2* | 10/2018 | Johnson | .................. G06F 19/00 |

(Continued)

FOREIGN PATENT DOCUMENTS

| | | |
|---|---|---|
| CN | 205647507 U | 10/2016 |
| CN | 107634774 A | 1/2018 |

OTHER PUBLICATIONS

Baum, "Smartwatch app to guide would-be good samaritans with CPR protocol," https://medcitynews.com/2015/01/smartwatch-app-helps-good-samaritans-cpr-protocol/, Jan. 23, 2015, pp. 1-9.

(Continued)

*Primary Examiner* — Tanmay K Shah
(74) *Attorney, Agent, or Firm* — Alexis N. Hatzis

(57) ABSTRACT

A method, computer system, and a computer program product for automated smart watch assistance is provided. The present invention may include detecting a distress signal from a sensor of a distressed user device. The present invention may then include broadcasting a cardiopulmonary resuscitation (CPR) request based on detecting the distress signal from the sensor of the distressed user device. The present invention may then include receiving a response to the broadcasted CPR request based on an altered direction of travel of a responding user device. The present invention may finally include establishing a connection between the distressed user device and the responding user device.

14 Claims, 8 Drawing Sheets

(56) References Cited

U.S. PATENT DOCUMENTS

| | | | |
|---|---|---|---|
| 2008/0004904 A1 | 1/2008 | Tran | |
| 2008/0171311 A1* | 7/2008 | Centen | G09B 23/288 |
| | | | 434/265 |
| 2014/0278229 A1 | 9/2014 | Hong et al. | |
| 2016/0018948 A1* | 1/2016 | Parvarandeh | G06F 1/169 |
| | | | 345/175 |
| 2016/0071392 A1 | 3/2016 | Hankey | |
| 2016/0100302 A1 | 4/2016 | Barash et al. | |
| 2017/0172424 A1* | 6/2017 | Eggers | A61B 5/0205 |
| 2017/0281462 A1* | 10/2017 | Freeman | A61H 31/005 |
| 2018/0092802 A1* | 4/2018 | Giacometti | A61H 31/005 |
| 2018/0221645 A1* | 8/2018 | Medema | A61N 1/39 |

OTHER PUBLICATIONS

Farooq, "PerfectCPR," https://watchaware.com/watch-apps/1109560255, Printed on Apr. 16, 2018, pp. 1-3.

Mell et al., "The NIST Definition of Cloud Computing," National Institute of Standards and Technology, U.S. Department of Commerce, Special Publication 800-145, Sep. 2011, pp. 1-7.

International Searching Authority, Notification of Transmittal of the International Search Report and the Written Opinion of the International Searching Authority, or the Declaration, dated Aug. 26, 2019, 9 pages, International Application No. PCT/IB2019/053918.

\* cited by examiner

AUTOMATED SMART WATCH ASSISTANCE IN THE EVENT OF CARDIAC ARREST

BACKGROUND

The present invention relates generally to the field of computing, and more particularly to wearable health devices.

Smart watches can assist in situations of cardiac arrest where cardiopulmonary resuscitation (CPR) is needed to revive a person. Smart watches may detect the impending presence of a heart related illness through the monitoring of a user's heart rate utilizing sensors embedded within the smart watch and may, if necessary, issue an alert if a heart related illness is detected. A smart watch may also assist in the act of performing compression CPR by utilizing sensors on a smart watch to monitor the movements a user makes during CPR administration and to ensure that the user is performing compression CPR at the correct pressure and rhythm.

SUMMARY

Embodiments of the present invention disclose a method, computer system, and a computer program product for automated smart watch assistance. The present invention may include detecting a distress signal from a sensor of a distressed user device. The present invention may then include broadcasting a cardiopulmonary resuscitation (CPR) request based on detecting the distress signal from the sensor of the distressed user device. The present invention may then include receiving a response to the broadcasted CPR request based on an altered direction of travel of a responding user device. The present invention may finally include establishing a connection between the distressed user device and the responding user device.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
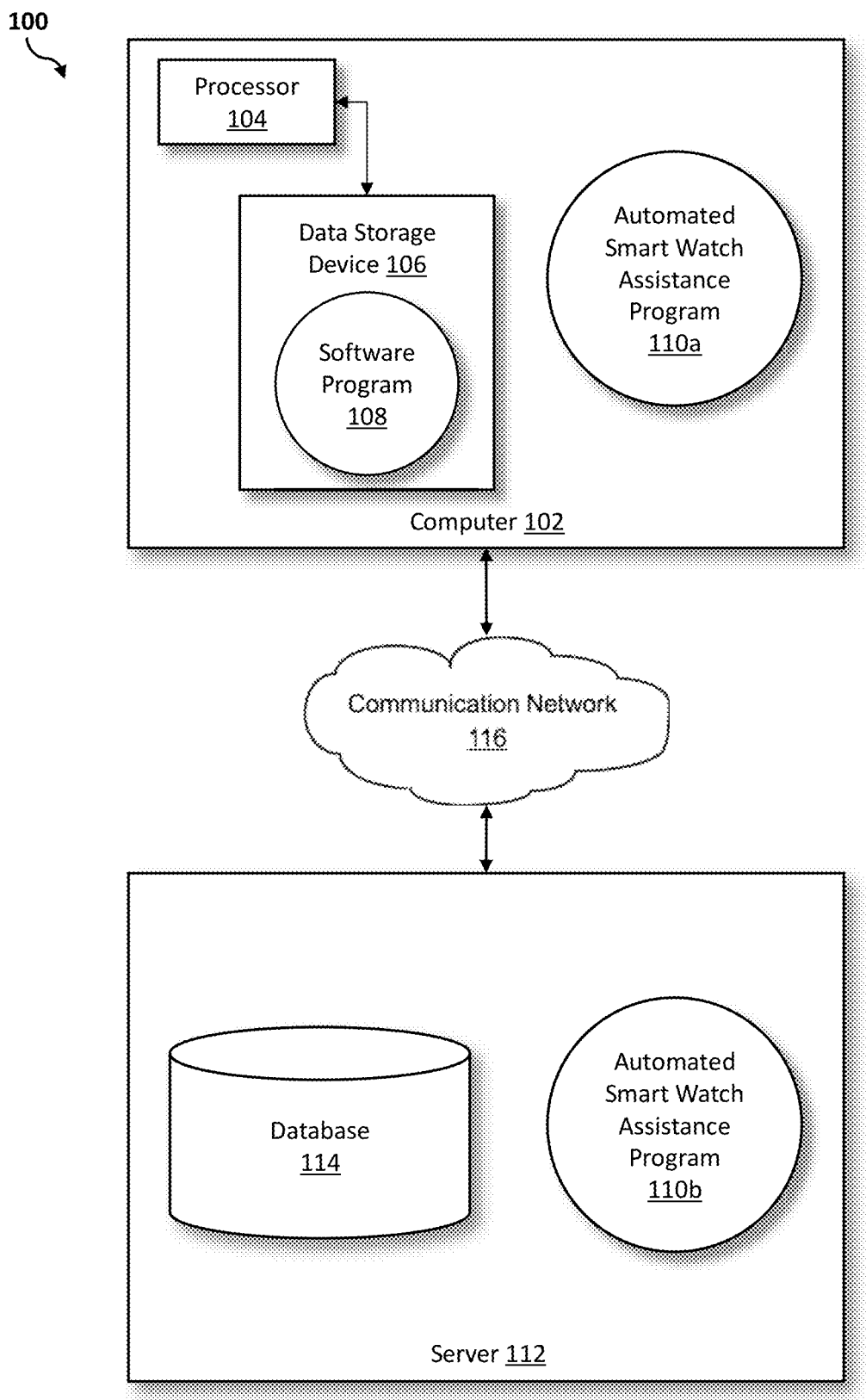
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for automated smart watch assistance. As such, the present embodiment has the capacity to improve the technical field of wearable health devices by automating smart watch assistance in the event of cardiac arrest. More specifically, the present invention may include detecting a distress signal from a sensor of a distressed user device. The present invention may then include broadcasting a cardiopulmonary resuscitation (CPR) request based on detecting the distress signal from the sensor of the distressed user device. The present invention may then include receiving a response to the broadcasted CPR request based on an altered direction of travel of a responding user device. The present invention may finally include establishing a connection between the distressed user device and the responding user device.

As described previously, smart watches can assist in situations of cardiac arrest where cardiopulmonary resuscitation (CPR) is needed to revive a person. Smart watches may detect the impending presence of a heart related illness through the monitoring of a user's heart rate utilizing sensors embedded within the smart watch, and may, if necessary, issue an alert if a heart related illness is detected. A smart watch may also assist in the act of performing compression CPR by utilizing sensors on a smart watch to monitor the movements a user makes during CPR administration and to ensure that the user is performing compression CPR at the correct pressure and rhythm.

When a person experiences cardiac arrest, people nearby may need to be alerted. Sounding an audible alarm when no pulse is detected may not be satisfactory because people hearing the alarm may not understand what the alarm signifies, people may not hear the alarm in busy areas or if wearing headphones, and people may not be able to locate the source of the alarm. Furthermore, when a person experiences cardiac arrest, every second of time is precious and a user attempting to administer CPR may not have the time to manually locate and launch a CPR assistance application on the user's smartphone or smart watch. Lastly, a user attempting to administer CPR may experience difficulty when checking for a pulse prior to performing compression CPR. In fact, researchers have concluded that a lay rescuer may not reliably detect the absence of a pulse in a timely fashion. Nevertheless, knowing when the heart has stopped and has restarted is critical to the performance of CPR.

Therefore it may be advantageous to, among other things, provide a solution that assists both victims of cardiac arrest and providers of CPR through a hands-free fully automated solution that announces the need for CPR, assists in the performance of CPR, and detects when a victim has regained a pulse and therefore CPR should be ceased.

According to at least one embodiment, a wearable may be used for automated cardiopulmonary resuscitation (CPR)

assistance, including but not limited to smart watches and/or other devices capable of gathering biometric and/or other sensor data of a user.

According to at least one embodiment, ultrasound communication may be used to alert nearby users to a cardiac event, even if the alerted user has no established relationship with a cardiac victim.

According to at least one embodiment, biometric information (e.g., biometric sensor data) from a cardiac victim's smart watch, including biometric readings recorded on the cardiac victim's smart watch, may be automatically provided to the smart watch of the person assisting the victim, without any prior pairing or manual intervention.

According to at least one embodiment, biometric and movement sensors on a smart watch may detect when a user is experiencing cardiac arrest. If a sufficient threshold is reached, based on the readings of the biometric and movement sensors, a CPR alarm may be rendered and communicated to nearby smart watches using ultrasound communication.

According to at least one embodiment, a nearby smart watch that receives an ultrasound communication may display the rendered CPR alert, which may provide information about the nature of the alert, the individual in need of help, and the location of the individual in relation to the receiving user. If the receiving user begins to move toward the alert location, a CPR assistance application may be automatically launched on the receiving user's smart watch.

According to at least one embodiment, the smart watch of a receiving user (e.g., an assisting user) and the smart watch of the victim may exchange an electronic handshake over ultrasound communication in order to establish a Bluetooth® (Bluetooth and all Bluetooth-based trademarks and logos are trademarks or registered trademarks of Bluetooth SIG, Inc. and/or its affiliates) pairing. The victim's smart watch may continue to monitor the victim's vital signs, and may communicate the victim's vital signs over the established (e.g., paired) Bluetooth® connection to the assisting user's smart watch. If the victim reestablishes a pulse, the assisting user may be informed of the victim's heart rate via a rendering on the assisting user's smart watch.

According to at least one embodiment, the automated smart watch assistance program may utilize ultrasound communication to broadcast a message to a nearby smart watch user, which message may indicate that a person may have experienced cardiac arrest. The communicated message may include information detailing the location of the cardiac arrest victim in addition to the cardiac arrest victim's distance from the message recipient.

According to at least one embodiment, the automated smart watch assistance program may automatically pair a smart watch of a cardiac arrest victim with a smart watch of a nearby (e.g., closely located) automated smart watch assistance program user (i.e., an assisting user) so that the cardiac arrest victim's biometric information, such as the presence or absence of a pulse, may be transmitted to the smart watch of the nearby automated smart watch assistance program user assisting with CPR (i.e., the assisting user).

According to at least one embodiment, the automated smart watch assistance program may be utilized by medical device manufacturers, healthcare providers and payers (e.g., hospitals and insurance companies), those responsible for public safety (e.g., police forces and fire departments), airports, mass transit operators, sports venues, mall operators, and smart watch manufacturers, among many other users.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an automated smart watch assistance program 110a. The networked computer environment 100 may also include a server 112 that is enabled to run an automated smart watch assistance program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 6, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the automated smart watch assistance program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the automated smart watch assistance program 110a, 110b (respectively) to automatically send biometric readings recorded on the smart watch of a victim to the smart watch of an assisting user without any prior pairing or manual intervention. The automated smart watch assistance method is explained in more detail below with respect to FIGS. 2 through 5.

Figure 2:
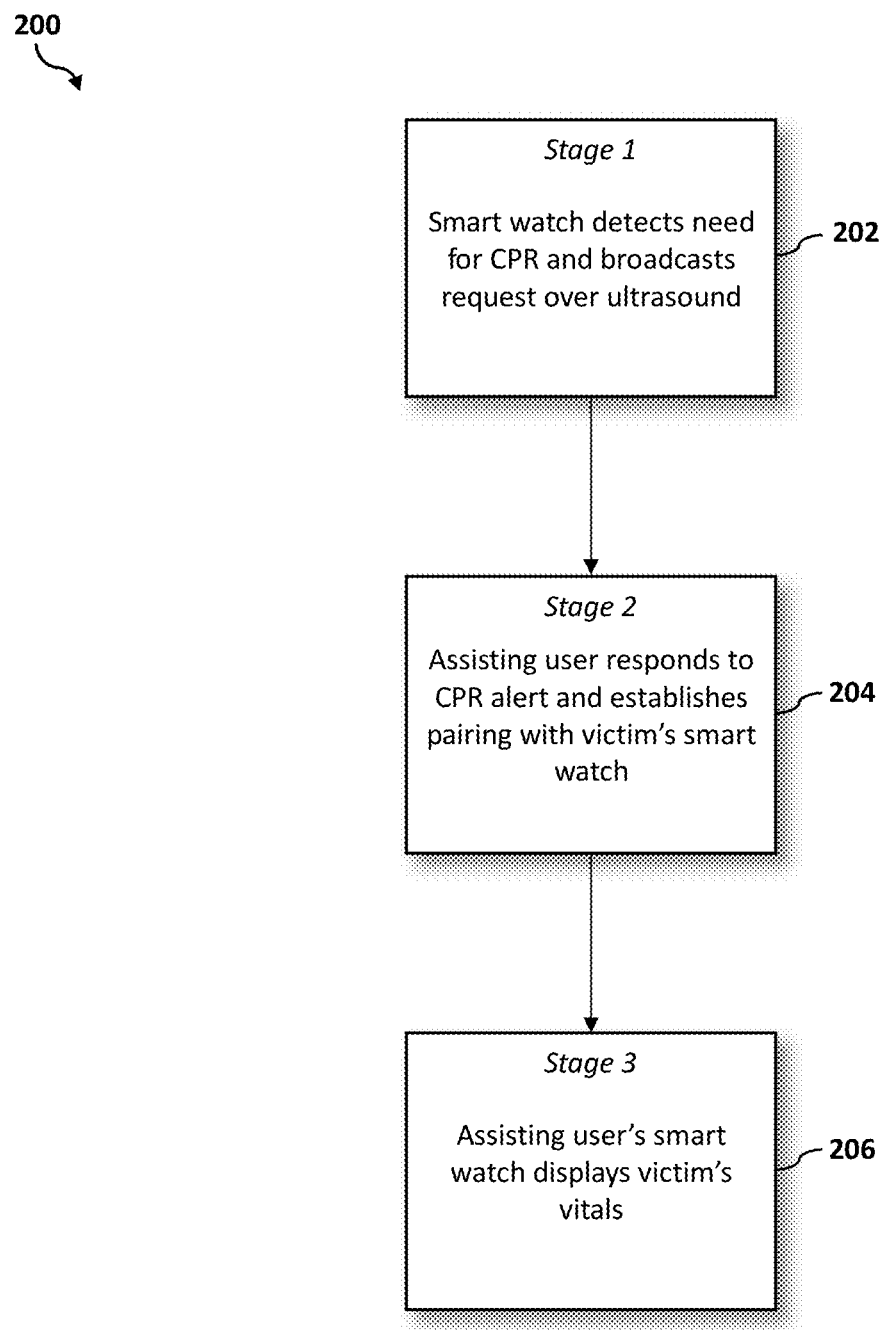
FIG. 2 is an operational flowchart illustrating a process for automated smart watch assistance according to at least one embodiment.

Referring now to FIG. 2, an operational flowchart illustrating the exemplary automated smart watch assistance process 200 used by the automated smart watch assistance program 110a and 110b according to at least one embodiment is depicted.

At 202, a user's smart watch detects the need for cardiopulmonary resuscitation (CPR) and broadcasts a request over ultrasound. This may be referred to as Stage 1 of the automated smart watch assistance program 110a, 110b, which may begin with a user signing up or opting in to participation in the automated smart watch assistance program 110a, 110b (i.e., user registration). User registration may be done using an Internet-connected computing device, including a mobile device or tablet, among other devices, and may include the user providing his or her personal information, including but not limited to name, birthday, height, weight, age, gender, any illnesses or ailments, whether the user is a smoker or nonsmoker, and a distinguishing photograph, which personal information and photograph may be sent to assisting users if a CPR alert is broadcasted. The user may input his or her personal information and photograph into the automated smart watch assistance program 110a, 110b interface at the designated areas specified for user input of personal information and photograph.

User registration may be completed by any person (e.g., male or female) of suitable age and discretion interested in participating in the automated smart watch assistance program 110a, 110b. User registration may include the downloading of an automated smart watch assistance program 110a, 110b mobile application onto the user's mobile device or tablet which is also compatible with, and may be downloaded onto, the user's smart watch.

A person of suitable age and discretion who completes a user registration for the automated smart watch assistance program 110a, 110b may become a registered user.

A smart watch worn by a registered user of the automated smart watch assistance program 110a, 110b may use various sensors to detect or determine whether a user may have experienced cardiac arrest, a loss of consciousness, and/or whether a smart watch user may need CPR. The various sensors used by the automated smart watch assistance program 110a, 110b may include but are not limited to including: biometric sensors, wherein a heart rate monitor may detect an abnormal heart rate and may ultimately detect the absence of a pulse; blood pressure sensors; skin temperature sensors; and movement sensors, wherein a smart watch accelerometer and/or gyroscope may detect a movement or absence thereof that may be consistent with a fall and/or a loss of consciousness.

The automated smart watch assistance program 110a, 110b may analyze sensor data to determine whether a user of the automated smart watch assistance program 110a, 110b has experienced cardiac arrest and/or may need CPR. Sensor data analyzed by the automated smart watch assistance program 110a, 110ba may be measured against (e.g., compared to) a predetermined threshold, which measurement or comparison may reduce the chance of falsely determining that a user of the automated smart watch assistance program 110a, 110b may be experiencing cardiac arrest and/or may need CPR (i.e., a false positive).

For example, regarding the threshold discussed above, a determination by a single sensor that a user of the automated smart watch assistance program 110a, 110b does not have a pulse may not be enough to trigger a call for help (e.g., to broadcast a request for CPR), since there may be several reasons why a user's pulse may not be detected by the user's smart watch, including but not limited to a faulty sensor, or a bad contact with the user's wrist. However, sensor data generated by more than one sensor and merged together to form a combined sensor database (i.e., database 114) may more accurately detect whether a user has met the predetermined threshold. For example, combined sensor data may detect an abnormal heart rate, followed by bodily movement consistent with a fall, followed by no measurable heart rate and/or blood pressure, and no further bodily movement. In this instance, the predetermined threshold may be met and/or exceeded and an alarm may be triggered.

When a predetermined threshold is met and an alarm is triggered, the automated smart watch assistance program 110a, 110b may prepare a CPR alert which may be a message broadcasted to all registered users of the automated smart watch assistance program 110a, 110b. A registered user of the automated smart watch assistance program 110a, 110b may have registered for participation in the automated smart watch assistance program 110a, 110b in the manner discussed previously, and may have downloaded the application onto the user's smart watch, where the application may now be running. A running version of the automated smart watch assistance program 110a, 110b may be listening for incoming ultrasound communications, as will be discussed in more detail below.

The broadcasted message (e.g., text message) may include profile information of the user in distress (i.e., a user profile), location information of the user in distress (i.e., user location), and other relevant information of the user in distress (i.e., user details). The user in distress may also be referred to as the victim. The user profile may include the user's name and picture, as well as any other personal information retrieved from the user's profile within the automated smart watch assistance program 110a, 110b. The user location may include the user's current location, as retrieved from the global positioning system (GPS) of the user's associated device (i.e., smart watch). The user details may include all other pertinent information concerning the user which may be relevant to a medical responder, including but not limited to the user's medical history, illnesses, allergies, asthmatic conditions, prescription medications, emergency contacts, primary care physician, and/or normal (i.e., baseline) vitals. The user details may be inputted into the automated smart watch assistance program 110a, 110b by the user upon registration and may be modified and/or supplemented at any time within the automated smart watch assistance program 110a, 110b interface. A user's baseline vitals may also be determined by the automated smart watch assistance program 110a, 110b based on any previously gathered sensor data which may be inputted into the automated smart watch assistance program 110a, 110b upon user registration.

The broadcasted CPR alert may be sent over ultrasound communication using an onboard speaker of a user's smart watch. Ultrasound communication may be a sound with frequency greater than 20 kHz and may be inaudible to the human ear. Although users of the automated smart watch assistance program 110a, 110b may not sense the ultrasound communication, the transmission may contain data encoded in ultrasound concerning the nature of the alert (e.g., the CPR alert), including the location of the victim, the victim's photograph and the victim's name. The location of the victim, the victim's photograph, and the victim's name may be used by an assisting user to locate a victim in a densely populated area (e.g., in a crowd). For example, a victim's photograph, used in combination with the location of the victim's distress signal, may enable immediate physical identification of a victim at a crowded concert by an assisting user.

If and/or when a Bluetooth® connection is made, any relevant medical information may be communicated to an assisting user, as discussed previously.

Nearby smart watches may receive the broadcasted CPR using an onboard microphone which may continually listen for ultrasound communications. No prior pairing between the device of the user in distress (i.e., the victim) and an assisting user may be required. Upon receiving an ultrasound communication, smart watches belonging to registered users of the automated smart watch assistance program 110a, 110b may render the CPR alert on the smart watch screen. Additionally, a registered user's smart watch may provide haptic and audible feedback to signal the smart watch user to the CPR alert. The rendering of a CPR alert on a user's smart watch will be discussed in more detail below with respect to FIG. 3.

Smart watches and other devices connected to the automated smart watch assistance program 110a, 110b, which are in receipt of the ultrasound communication, may act as a repeater, and may pass the signal on to other connected devices. A repeater may be an electronic device that receives a signal and retransmits it, which may be used to extend the signal's distance. For example, a mobile phone may receive a CPR alert over ultrasound communication and may use an onboard speaker to repeat the ultrasound signal, which may result in an extended range and reach of the broadcasted CPR alert.

At 204, an assisting user responds to the CPR alert and establishes a pairing with the victim's smart watch. This may be referred to as Stage 2 of the automated smart watch assistance program 110a, 110b. Here, the victim's smart watch may monitor the movement and direction of travel of users of the smart watch assistance program 110a, 110b, after a CPR alert message has been rendered. If the smart watch of the victim (i.e., the user in distress) detects that another user of the automated smart watch assistance program 110a, 110b is traveling in the direction of the victim, then that user becomes an assisting user who is responding to the CPR alert. The assisting user may need to merely change his or her direction of travel towards the location of the victim to be deemed an assisting user who may be responding to the broadcasted CPR alert.

For example, once a CPR request has been broadcasted, based on a determination that the victim is in distress, then any altered direction of travel of another user of the automated smart watch assistance program 110a, 110b which is towards the location of the victim may be sufficient to deem the other user an assisting user.

When a smart watch of an assisting user determines that the assisting user is assisting the victim, a CPR assistance guide may be launched on the assisting user's smart watch, either within the automated smart watch assistance program 110a, 110b or by utilizing a third-party application on the assisting user's smart watch or connected mobile device. The CPR assistance guide may aid in the performance of compression CPR, including by monitoring the CPR technique, by issuing guidance based on the monitoring, and optionally, by placing a call to 911 to alert emergency services to the victim's condition and to receive live verbal CPR instructions. The CPR assistance guide may function by utilizing an accelerometer, any haptic feedback, and a gyroscope of the assisting user's smart watch, among other features, to indicate when a compression should be performed.

When an assisting user's smart watch detects that the user is located at the same physical location as the automated smart watch assistance program 110a, 110b victim, then the assisting user's smart watch may send an ultrasound communication to the victim's smart watch, wherein the assisting user's smart watch requests a Bluetooth® (Bluetooth and all Bluetooth-based trademarks and logos are trademarks or registered trademarks of Bluetooth SIG, Inc. and/or its affiliates) pairing. The automated smart watch assistance program 110a, 110b may determine that an assisting user is located at the same location as the victim based on a comparison of the GPS location of the broadcasted CPR alert and the GPS location of the assisting user. When a microphone of the victim's smart watch detects the Bluetooth® pairing request, an electronic handshake signal is exchanged and the Bluetooth® pairing is performed. A pairing of devices will be discussed in more detail below with respect to FIG. 4.

If multiple assisting users arrive to assist the victim, a Bluetooth® pairing may be established with the smart watch of the victim and the smart watches of all assisting users. Two-way communication may be established between Bluetooth® connected devices, which may be beneficial for both the victim and assisting user(s) as compared to the one-way broadcast of ultrasound communication. The CPR assistance guide instructions, as discussed previously, may be sent to all assisting users. The vital signs of the victim, as discussed previously, and as will be discussed in more detail below with respect to step 206, may also be sent to all assisting users.

At 206, the assisting user's smart watch displays the victim's vitals (i.e., a vital sign). This may be referred to as Stage 3 of the automated smart watch assistance program 110a, 110b. A paired Bluetooth® connection may be established between the assisting user's smart watch and the smart watch worn by the victim, as described previously, by utilizing a two-way electronic handshake over ultrasound communication.

Despite the victim's condition, the victim's smart watch may continue to monitor the victim's vital signs, including but not limited to the victim's heart rate (i.e., a heart rate value) the victim's blood pressure (i.e., a blood pressure value), the victim's body temperature (i.e., a body temperature value), the victim's respiration rate (i.e., a breathing rate), and/or any other medical conditions of the victim, and may send the victim's vital signs over the paired connection to the assisting user's smart watch. The assisting user may utilize the paired connection and any vital signs received from the victim's smart watch, to establish that the victim has no pulse, and that CPR should commence. The paired Bluetooth® connection may continue while CPR is being given, and may also continue while an Automated External Defibrillator (AED) may be used to attempt to revive the victim.

If the victim reestablishes a pulse, a notification may be created, which notification may be rendered on the assisting user's smart watch. If there is more than one assisting user, a notification may be rendered on the smart watch of each assisting user. The notification may indicate that the victim's pulse has been reestablished and that the assisting user may cease CPR and/or AED. The notification may be visual, haptic, and/or audible to ensure that the notification captures the user or users' attention. A rendered notification will be discussed in more detail below with respect to FIG. 5.

After a predefined period of time for which the victim is deemed to have a reestablished and normal pulse based on acceptable medical ranges, which period of time may be automatically configured within the automated smart watch assistance program 110a, 110b interface, the connection between the assisting user's smart watch and the victim's smart watch may be disconnected and the pairing may be removed. A user's normal heart rate, based on acceptable medical ranges, may be determined by the automated smart watch assistance program 110a, 110b based on the user's inputted personal information, including age, height, weight, whether the user is a smoker or nonsmoker, and any preexisting medical conditions, among other factors.

For example, the automated smart watch assistance program 110a, 110b may be configured to disconnect a Bluetooth® connection when the victim is determined to have a reestablished pulse lasting for three minutes, and the victim's pulse is determined to be within an acceptable medical range given the user's inputted personal information.

Figure 3:
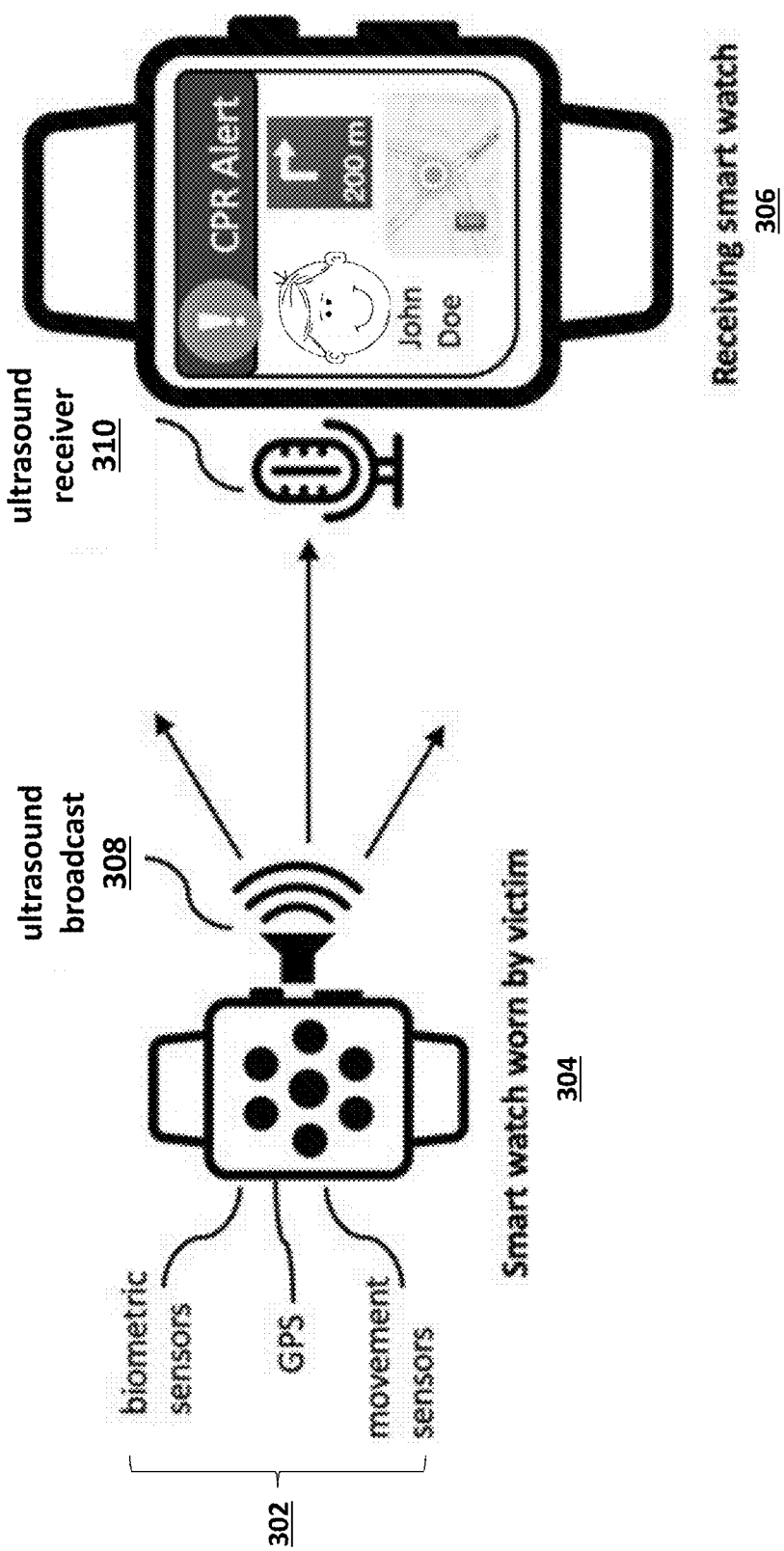
FIG. 3 illustrates a rendering of a CPR alert according to at least one embodiment.

Referring now to FIG. 3, the rendering of a CPR alert according to at least one embodiment is depicted. The automated smart watch assistance program 110a, 110b may provide for haptic and audible feedback to signal the smart watch user that there is a CPR alert. As described previously, GPS location, biometric sensors, and movement sensors 302 may gather data from the victim's smart watch 304 and may communicate the gathered data to the assisting user's smart watch 306 using ultrasound communication 308 (i.e., ultrasound broadcast). An ultrasound receiver 310 on the assisting user's device (i.e., the receiving smart watch 306) may pick up signals sent using ultrasound communication 308 from the victim's smart watch.

Figure 4:
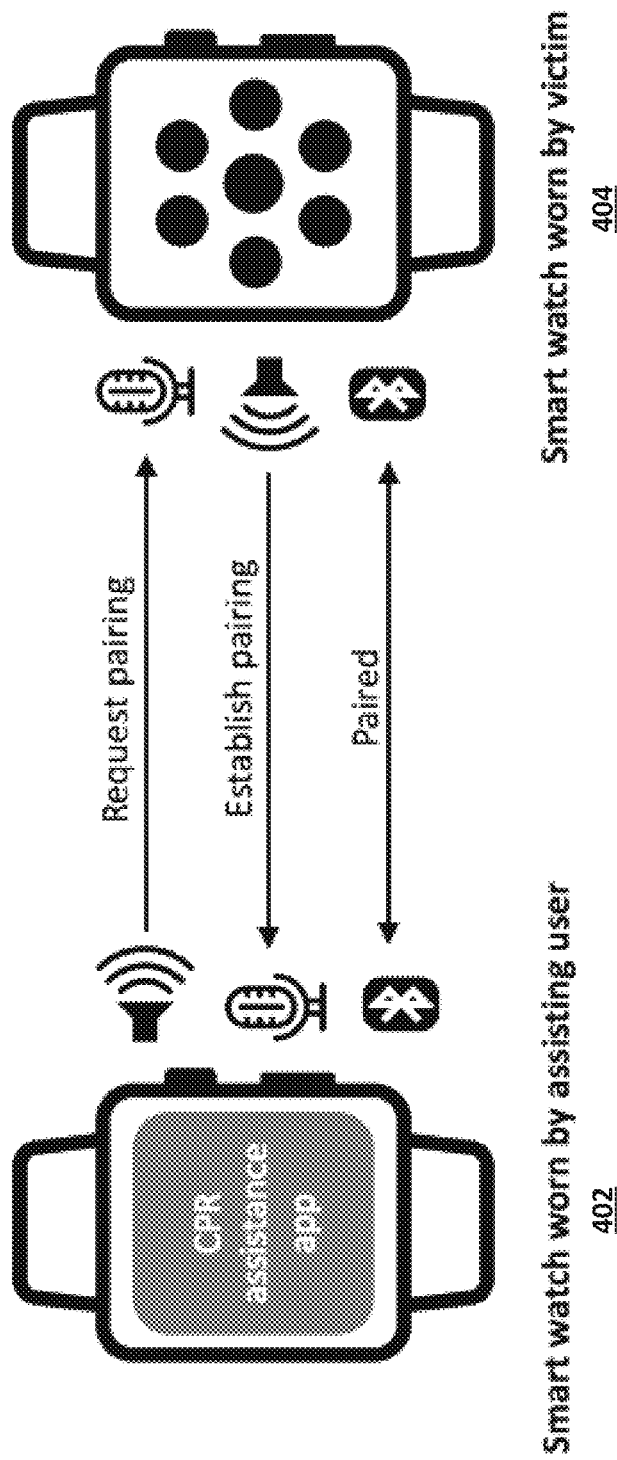
FIG. 4 illustrates a pairing of devices according to at least one embodiment.

Referring now to FIG. 4 the pairing of devices according to at least one embodiment is depicted. A Bluetooth® connection may be established when a user of the automated smart watch assistance program 110a, 110b travels in the direction of the victim, which connection may enable CPR assistance to commence. To establish a Bluetooth® connection, the assisting user's smart watch 402 may request a pairing, and an electronic handshake signal between the assisting user's smart watch 402 and the victim's smart watch 404 may be exchanged.

Figure 5:
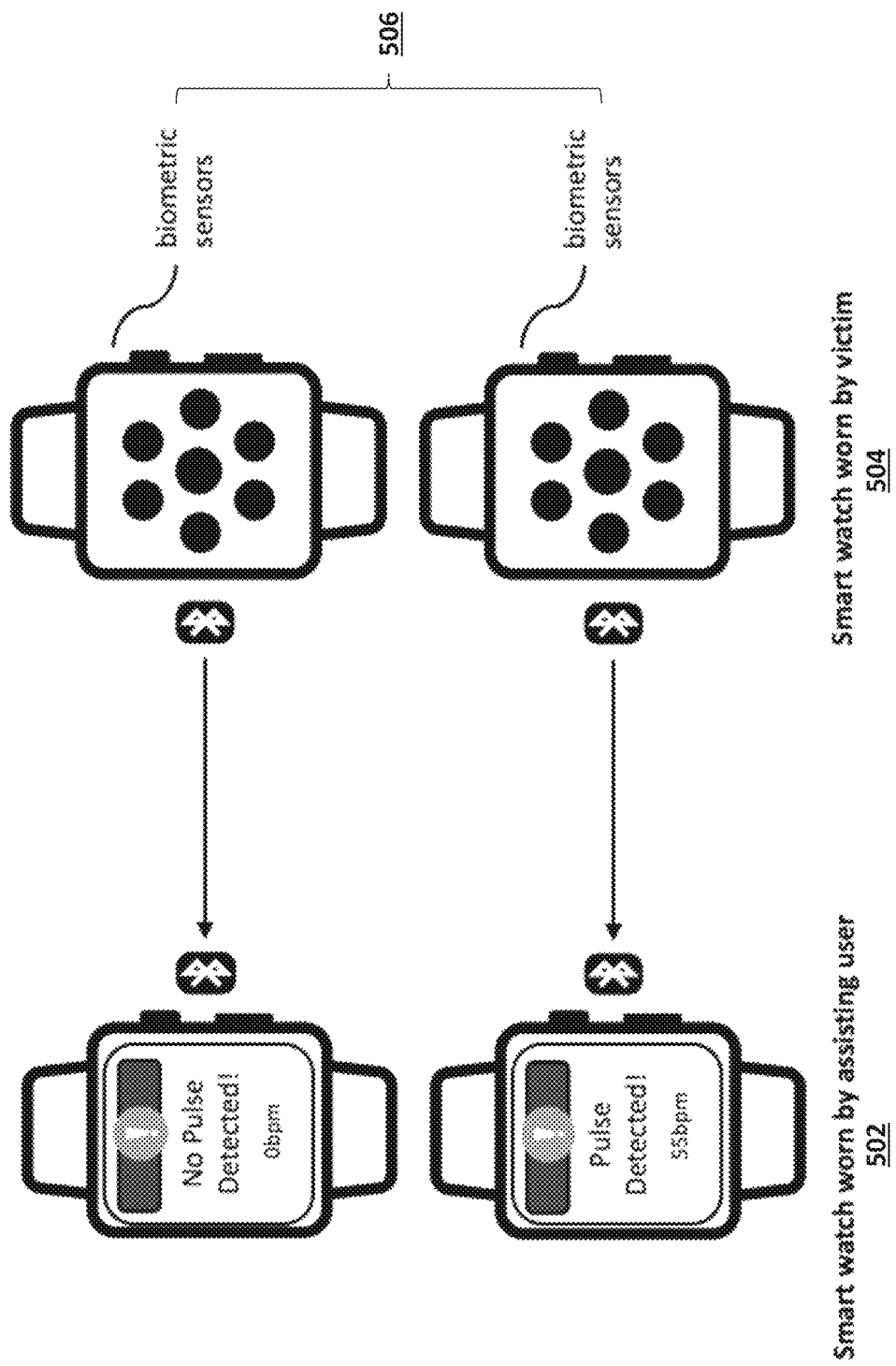
FIG. 5 illustrates a rendered notification according to at least one embodiment.

Referring now to FIG. 5 a rendered notification according to at least one embodiment is depicted. Once a Bluetooth® connection has been established between the assisting user's smart watch 502 and the victim's smart watch 504, the smart watch worn by the assisting user 502 may display the victim's reestablished pulse, based on readings generated by biometric sensors 506 located on the victim's smart watch 504 and communicated over Bluetooth® connection to the assisting user's smart watch 502.

It may be appreciated that FIGS. 2 through 5 provide only an illustration of one embodiment and do not imply any limitations with regard to how different embodiments may be implemented. Many modifications to the depicted embodiment(s) may be made based on design and implementation requirements.

According to at least one alternate embodiment, there may be a requirement of CPR training for assisting users of the automated smart watch assistance program 110a, 110b. In this instance, proof of CPR certification may be required on registration. Proof of CPR certification may be uploaded via a web portal or mobile application, and/or radio buttons may be toggled within the web portal or mobile application to indicate an automated smart watch assistance program 110a, 110b user's level of training, experience and expertise with CPR.

According to at least one alternate embodiment, an assisting user may assist a victim by finding a third party who may not be registered for the automated smart watch assistance program 110a, 110b but who may be certified in CPR or otherwise willing and/or qualified to assist the victim and administer CPR. The assisting user who is registered for the automated smart watch assistance program 110a, 110b (i.e., the registered assisting user) may join the nonregistered third party in traveling to the victim so that the location of the registered assisting user may be noted by the automated smart watch assistance program 110a, 110b and a connection may be established between the smart watch of the registered assisting user and the smart watch of the victim, thereby permitting both CPR assistance to be displayed on, and the victim's vitals to be sent to, the registered assisting user's smart watch.

According to at least one alternate embodiment, the automated smart watch assistance program 110a, 110b may monitor a user's sensor data, including but not limited to the user's heart rate, as compared to acceptable medical standards, and may alert the user via a notification on the user's smart watch or via a notification on the automated smart watch assistance program 110a, 110b interface that a potential illness is detected and the user should seek medical assistance.

Figure 6:
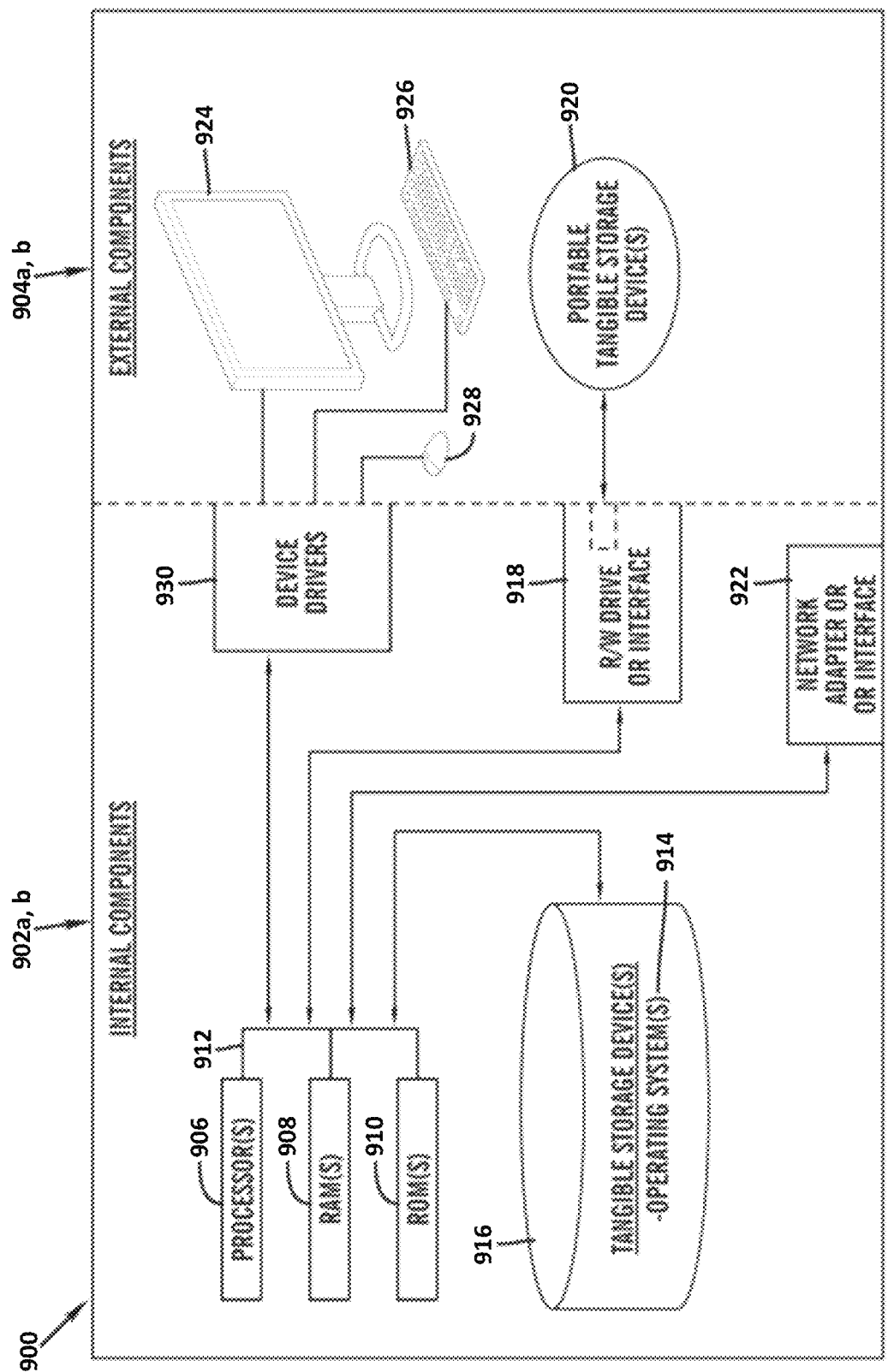
FIG. 6 is a block diagram of internal and external components of computers and servers depicted in FIG. 1 according to at least one embodiment.

FIG. 6 is a block diagram 900 of internal and external components of computers depicted in FIG. 1 in accordance with an illustrative embodiment of the present invention. It should be appreciated that FIG. 6 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 6. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the automated smart watch assistance program 110a in client computer 102, and the automated smart watch assistance program 110b in network server 112, may be stored on one or more computer-readable tangible storage devices 916 for execution by one or more processors 906 via one or more RAMs 908 (which typically include cache memory). In the embodiment illustrated in FIG. 6, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the automated smart watch assistance program 110a and 110b can be stored on one or more of the respective portable computer-readable tangible storage devices 920, read via the respective R/W drive or interface 918 and loaded into the respective hard drive 916.

Each set of internal components 902 *a, b* may also include network adapters (or switch port cards) or interfaces 922 such as a TCP/IP adapter cards, wireless wi-fi interface cards, or 3G or 4G wireless interface cards or other wired or wireless communication links. The software program 108 and the automated smart watch assistance program 110*a* in client computer 102 and the automated smart watch assistance program 110*b* in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the automated smart watch assistance program 110*a* in client computer 102 and the automated smart watch assistance program 110*b* in network server computer 112 are loaded into the respective hard drive 916. The network may comprise copper wires, optical fibers, wireless transmission, routers, firewalls, switches, gateway computers and/or edge servers.

Each of the sets of external components 904 *a, b* can include a computer display monitor 924, a keyboard 926, and a computer mouse 928. External components 904 *a, b* can also include touch screens, virtual keyboards, touch pads, pointing devices, and other human interface devices. Each of the sets of internal components 902 *a, b* also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
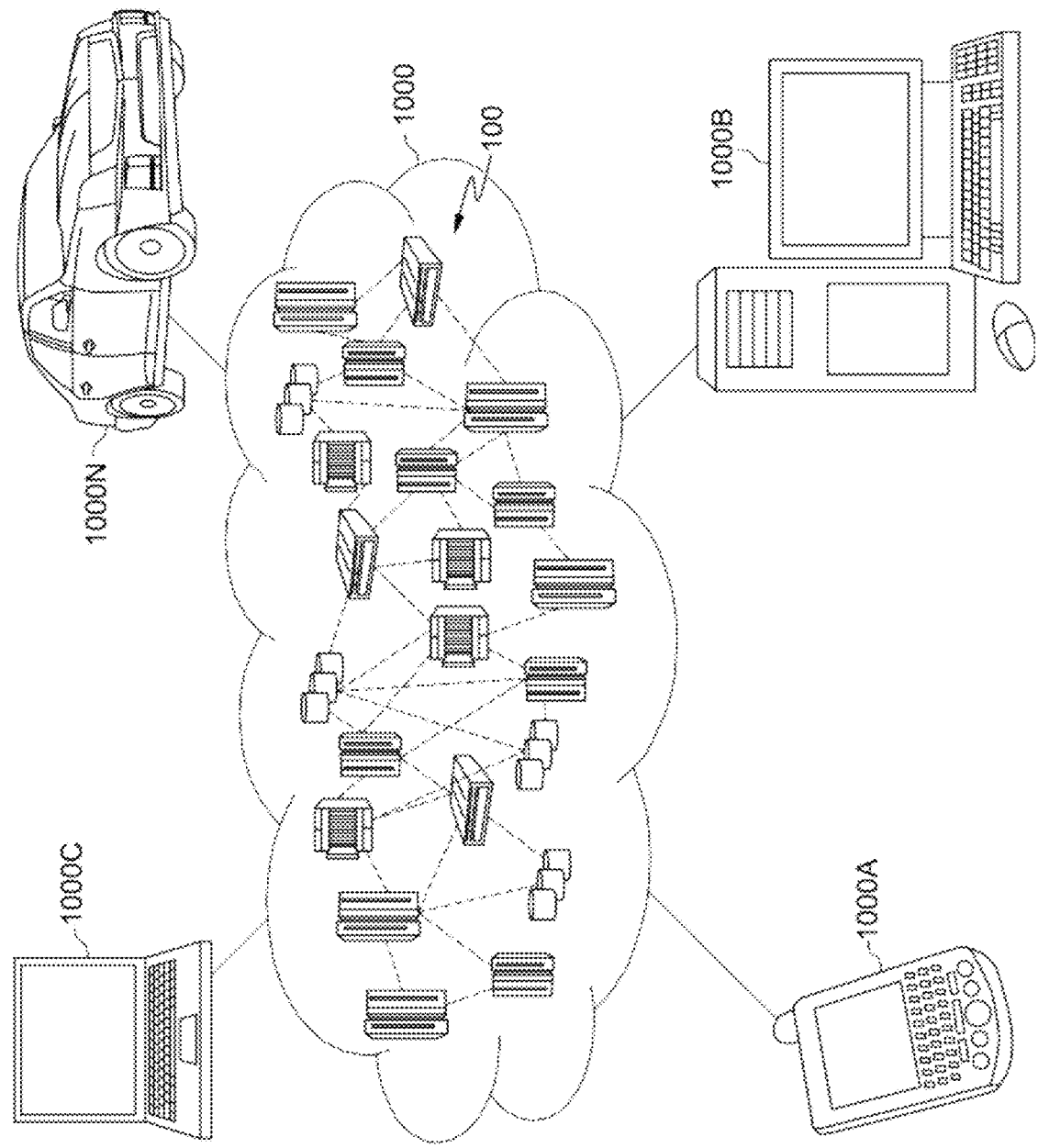
FIG. 7 is a block diagram of an illustrative cloud computing environment including the computer system depicted in FIG. 1, in accordance with an embodiment of the present disclosure.

Referring now to FIG. 7, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 7 are intended to be illustrative only and that computing nodes 100 and cloud computing environment 1000 can communicate with any type of computerized device over any type of network and/or network addressable connection (e.g., using a web browser).

Figure 8:
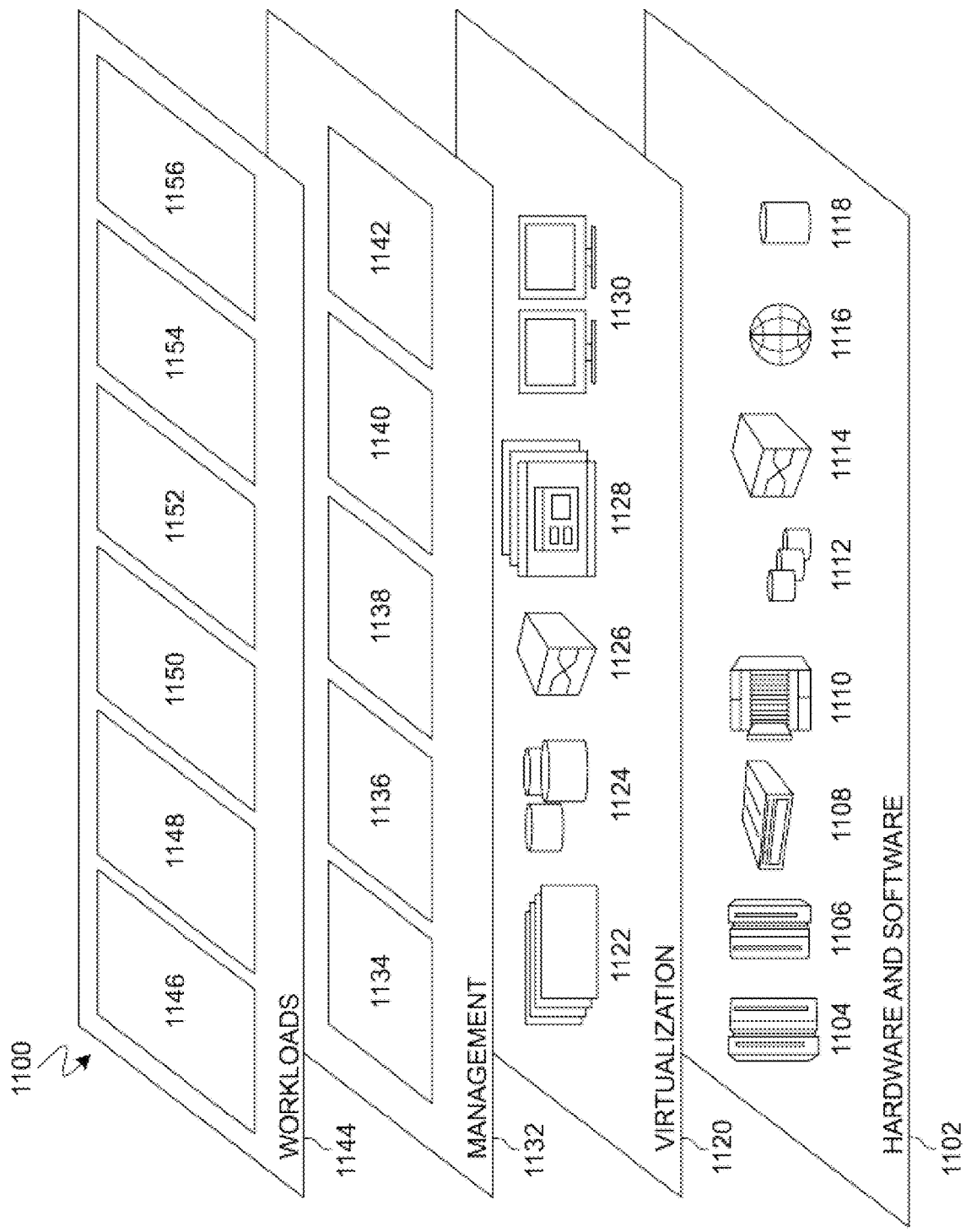
FIG. 8 is a block diagram of functional layers of the illustrative cloud computing environment of FIG. 7, in accordance with an embodiment of the present disclosure.

Referring now to FIG. 8, a set of functional abstraction layers 1100 provided by cloud computing environment 1000 is shown. It should be understood in advance that the components, layers, and functions shown in FIG. 8 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and automated smart watch assistance 1156. An automated smart watch assistance program 110a, 110b provides a way to automatically send biometric readings recorded on the smart watch of a victim to the smart watch of an assisting user without any prior pairing or manual intervention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automated wearable assistance, the method comprising:

detecting, by a sensor of a distressed user device, a distress signal;

broadcasting, by the distressed user device, a cardiopulmonary resuscitation (CPR) request based on detecting the distress signal from the sensor of the distressed user device, wherein the broadcasted CPR request is sent over ultrasound communication using an onboard speaker of the distressed user device, and wherein the broadcasted CPR request is repeated using an onboard speaker of one or more connected devices:

receiving, by the distressed user device, a response from another automated wearable assistance device, to the broadcasted CPR request based on an altered direction of travel, as evidenced by a modified global positioning system (GPS) location of a responding user device;

wherein the altered direction is towards the distress user device; and sending a vital sign, by the distressed user device, to the responding user;

wherein the vital sign of the distressed user device is selected from the group of a heart rate value, a blood pressure value, and a body temperature value; and establishing a connection, by the distressed user device, between the distressed user device and the responding user device.

2. The method of claim 1, wherein detecting, by the sensor of the distressed user device, the distress signal further comprises:

monitoring a heart rate using a biometric sensor of the distressed user device.

3. The method of claim 1, wherein the broadcasted cardiopulmonary resuscitation (CPR) request is received over ultrasound communication using an onboard microphone of the responding user device.

4. The method of claim 1, wherein the broadcasted cardiopulmonary resuscitation (CPR) request further comprises a name of the user in distress, a photograph of the user in distress, a medical history of the user in distress, and a location of the user in distress.

5. The method of claim 1, wherein the connection between the distressed user device and the responding user device is established by exchange of electronic handshake using ultrasound communication.

6. A computer system for automated smart watch assistance, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

detecting, by a sensor of a distressed user device, a distress signal;

broadcasting, by the distressed user device, a cardiopulmonary resuscitation (CPR) request based on detecting the distress signal from the sensor of the distressed user device, wherein the broadcasted CPR request is sent over ultrasound communication using an onboard speaker of the distressed user device, and wherein the broadcasted CPR request is repeated using an onboard speaker of one or more connected devices;

receiving, by the distressed user device, a response from another automated wearable assistance device, to the broadcasted CPR request based on an altered direction of travel, as evidenced by a modified global positioning system (GPS) location of a responding user device;

wherein the altered direction is towards the distress user device; and establishing a connection, by the distressed user device, between the distressed user device and the responding user device; and sending, by the distressed user device, a vital sign of the distressed user device to the responding user device;

wherein the vital sign of the distressed user device is selected from the group of a heart rate value, a blood pressure value, and a body temperature value.

7. The computer system of claim 6, wherein detecting, by the sensor of the distressed user device, the distress signal further comprises:

monitoring a heart rate using a biometric sensor of the distressed user device.

8. The computer system of claim 6, wherein the broadcasted cardiopulmonary resuscitation (CPR) request is received over ultrasound communication using an onboard microphone of the responding user device.

9. The computer system of claim 6, wherein the broadcasted cardiopulmonary resuscitation (CPR) request further comprises a name of the user in distress, a photograph of the user in distress, a medical history of the user in distress, and a location of the user in distress.

10. The computer system of claim 6, wherein the connection between the distressed user device and the responding user device is established by exchange of electronic handshake using ultrasound communication.

11. A computer program product for automated smart watch assistance, comprising:

one or more computer-readable storage media and program instructions stored on at least one of the one or more tangible storage media, the program instructions executable by a processor to cause the processor to perform a method comprising:

detecting, by a sensor of a distressed user device, a distress signal;

broadcasting, by the distressed user device, a cardiopulmonary resuscitation (CPR) request based on detecting the distress signal from the sensor of the distressed user device, wherein the broadcasted CPR request is sent over ultrasound communication using an onboard speaker of the distressed user device;

receiving, by the distressed user device, to the broadcasted CPR request based on an altered direction of travel, as evidenced by a modified global positioning system (GPS) location of a responding user device;

establishing a connection, by the distressed user device, between the distressed user device and the responding user device; and sending, by the distressed user device, a vital sign of the distressed user device to the responding user device;

wherein the vital sign of the distressed user device is selected from the group of a heart rate value, a blood pressure value, and a body temperature value.

12. The computer program product of claim 11, wherein detecting the distress signal from the sensor of the distressed user device further comprises:

monitoring a heart rate of the distressed user device based on a biometric sensor.

13. The computer program product of claim 11, wherein the broadcasted cardiopulmonary resuscitation (CPR) request is received over ultrasound communication using an onboard microphone of the responding user device.

14. The computer program product of claim 11, wherein the connection between the distressed user device and the responding user device is established by exchange of electronic handshake using ultrasound communication.

* * * * *